United States Patent
Yazdandoost et al.

(10) Patent No.: US 9,607,203 B1
(45) Date of Patent: Mar. 28, 2017

(54) BIOMETRIC SENSING DEVICE WITH DISCRETE ULTRASONIC TRANSDUCERS

(71) Applicant: Apple Inc., Cupertino, CA (US)

(72) Inventors: Mohammad Yeke Yazdandoost, Waterlo (CA); Jean-Marie Bussat, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 14/596,932

(22) Filed: Jan. 14, 2015

Related U.S. Application Data

(60) Provisional application No. 62/057,354, filed on Sep. 30, 2014.

(51) Int. Cl.
  *G06K 9/00* (2006.01)
  *A61B 5/1172* (2016.01)

(52) U.S. Cl.
  CPC .......... *G06K 9/0002* (2013.01); *A61B 5/1172* (2013.01)

(58) Field of Classification Search
  CPC .............................. G06K 9/0002; A61B 5/1172
  USPC ............. 382/115–125; 340/5.82, 5.83; 902/3
  See application file for complete search history.

(56) References Cited

U.S. PATENT DOCUMENTS

| | | | |
|---|---|---|---|
| 4,729,128 A | 3/1988 | Grimes | |
| 5,162,618 A | 11/1992 | Knowles | |
| 5,381,696 A | 1/1995 | Ichinose | |
| 5,515,298 A | 5/1996 | Bicz | |
| 5,589,636 A | 12/1996 | Bicz | |
| 5,719,950 A | 2/1998 | Osten | |
| 6,091,406 A | 7/2000 | Kambara | |
| 6,159,149 A * | 12/2000 | Erikson ................ | A61B 8/4483 600/437 |
| 6,720,712 B2 | 4/2004 | Scott | |
| 7,032,454 B2 | 4/2006 | Amano | |
| 7,400,750 B2 | 7/2008 | Nam | |
| 7,458,268 B2 | 12/2008 | Schneider et al. | |
| 7,497,120 B2 | 3/2009 | Schneider et al. | |
| 7,568,391 B2 | 8/2009 | Schneider et al. | |
| 7,656,932 B2 | 2/2010 | Durand | |
| 7,667,374 B2 * | 2/2010 | Aono .................... | B06B 1/0292 310/309 |
| 7,734,435 B2 | 6/2010 | Thomas et al. | |
| 7,739,912 B2 | 6/2010 | Schneider et al. | |
| 7,770,456 B2 | 8/2010 | Stevenson et al. | |
| 8,047,995 B2 | 11/2011 | Wakabayashi et al. | |

(Continued)

FOREIGN PATENT DOCUMENTS

WO    WO 94/02911    2/1994

*Primary Examiner* — Daniel Mariam
(74) *Attorney, Agent, or Firm* — Brownstein Hyatt Farber Schreck, LLP

(57) ABSTRACT

A biometric sensing system includes discrete ultrasonic transducers, a first electrode layer disposed over a first surface of the discrete ultrasonic transducers, and a second electrode layer disposed over a second surface of the discrete ultrasonic transducers. The first electrode layer includes discrete electrode members. Each discrete electrode member spans two or more discrete ultrasonic transducers. The second electrode layer includes discrete electrode elements, with a discrete electrode element disposed over the second surface of one ultrasonic transducer. Drive circuitry is operably connected to the first electrode layer, and readout circuitry is operably connected to the second electrode layer.

20 Claims, 10 Drawing Sheets

(56) References Cited

U.S. PATENT DOCUMENTS

| | | |
|---|---|---|
| 8,054,203 B2 | 11/2011 | Breed et al. |
| 8,085,998 B2 | 12/2011 | Setlak et al. |
| 8,095,328 B2 | 1/2012 | Thomas et al. |
| 8,179,678 B2 | 5/2012 | Yamashita et al. |
| 8,201,739 B2 | 6/2012 | Schneider et al. |
| 8,335,356 B2 | 12/2012 | Schmitt |
| 8,345,508 B2 | 1/2013 | Wodnicki et al. |
| 8,508,103 B2 | 8/2013 | Schmitt et al. |
| 8,536,465 B2 | 9/2013 | Hagiwara et al. |
| 8,601,876 B2 | 12/2013 | Schneider et al. |
| 8,617,078 B2 | 12/2013 | Machida et al. |
| 8,666,126 B2 | 3/2014 | Lee et al. |
| 8,724,869 B2 | 5/2014 | Schneider et al. |
| 8,781,180 B2 | 7/2014 | Schneider et al. |
| 8,791,792 B2 | 7/2014 | Benkley, III |
| 8,982,089 B2 | 3/2015 | Lim |
| 9,044,171 B2 | 6/2015 | Venkatraman et al. |
| 9,056,082 B2 | 6/2015 | Liautaud et al. |
| 9,100,034 B2 * | 8/2015 | Oshima ............... H03M 1/1038 |
| 9,132,693 B2 | 9/2015 | Klootwijk et al. |
| 9,170,668 B2 | 10/2015 | Schneider et al. |
| 9,323,393 B2 | 4/2016 | Djordjev et al. |
| 9,465,972 B2 | 10/2016 | Chung et al. |
| 2003/0102777 A1 | 6/2003 | Kuniyasu et al. |
| 2003/0109993 A1 | 6/2003 | Peat et al. |
| 2004/0140735 A1 | 7/2004 | Scott et al. |
| 2006/0196271 A1 | 9/2006 | Jancsik et al. |
| 2007/0222338 A1 * | 9/2007 | Aono ................... B06B 1/0292 310/334 |
| 2008/0142571 A1 | 6/2008 | Yokozuka et al. |
| 2008/0175450 A1 | 7/2008 | Scott |
| 2009/0058228 A1 * | 3/2009 | Wakabayashi ........ B06B 1/0292 310/334 |
| 2009/0167704 A1 | 7/2009 | Terlizzi et al. |
| 2012/0092026 A1 | 4/2012 | Liautaud et al. |
| 2012/0316445 A1 * | 12/2012 | Machida ............... B06B 1/0292 600/459 |
| 2013/0015868 A1 | 1/2013 | Peng |
| 2013/0278111 A1 * | 10/2013 | Sammoura .......... H01L 41/0926 310/317 |
| 2014/0333328 A1 | 11/2014 | Nelson et al. |
| 2014/0352440 A1 | 12/2014 | Fennell et al. |
| 2014/0355381 A1 | 12/2014 | Lal et al. |
| 2014/0359757 A1 * | 12/2014 | Sezan ..................... G06F 21/32 726/19 |
| 2015/0053006 A1 | 2/2015 | DeCoux et al. |
| 2015/0189136 A1 | 7/2015 | Chung et al. |
| 2015/0192547 A1 | 7/2015 | Lee et al. |
| 2015/0358740 A1 | 12/2015 | Tsai et al. |
| 2016/0063300 A1 | 3/2016 | Du et al. |
| 2016/0117541 A1 | 4/2016 | Lu et al. |

* cited by examiner

BIOMETRIC SENSING DEVICE WITH DISCRETE ULTRASONIC TRANSDUCERS

CROSS-REFERENCE TO RELATED APPLICATION

This application claims the benefit under 35 U.S.C. §119 (e) of U.S. Provisional Patent Application No. 62/057,354, filed Sep. 30, 2014, entitled "Biometric Sensing Device with Discrete Ultrasonic Transducers," the entirety of which is incorporated herein by reference.

TECHNICAL FIELD

The present invention relates to biometric sensing devices, and more particularly to a biometric sensing device that includes discrete ultrasonic transducers.

BACKGROUND

Many electronic devices, networks, and physical buildings include security features to prevent unauthorized access. For example, an electronic device can include a biometric sensing device, such as a fingerprint sensing device, that is used to verify a user's identity by determining whether captured biometric data matches known biometric data of an authorized user. The user is given access to the electronic device when the captured biometric data matches the known biometric data.

The performance of some biometric sensing devices may be adversely affected by conditions unrelated to the biometric sensing device itself. For example, a fingerprint sensing device can be sensitive to contaminants on a user's finger. Contaminants such as grease, lotion, dirt, sweat, and food particles on a finger can degrade a captured fingerprint image, which can prevent a fingerprint sensing device from matching the captured fingerprint image to a known fingerprint image. Alternatively, a finger contacting an input surface of the fingerprint sensing device with too much or too little pressure can reduce the quality of the captured fingerprint image and prevent the fingerprint sensing device from recognizing the user.

SUMMARY

Embodiments described herein provide an ultrasonic biometric sensing device. In one aspect, a biometric sensing system can include discrete ultrasonic transducers, a first electrode layer disposed over a first surface of the discrete ultrasonic transducers, and a second electrode layer disposed over a second surface of the discrete ultrasonic transducers. The first electrode layer includes discrete electrode members. Each discrete electrode member spans two or more discrete ultrasonic transducers. The second electrode layer includes discrete electrode elements, with a discrete electrode element disposed over the second surface of one ultrasonic transducer. High voltage drive circuitry is operably connected to the first electrode layer, and low voltage readout circuitry is operably connected to the second electrode layer. In one embodiment, at least a portion of the high voltage drive circuitry is included in a first integrated circuit operably connected to the first electrode layer, and at least a portion of the low voltage readout circuitry is included in a second integrated circuit positioned below and operably connected to the second electrode layer. The second integrated circuit can be a support structure for the discrete ultrasonic transducers.

In another aspect, an electronic device can include an ultrasonic biometric sensing device and an upper element that includes at least one layer of material disposed over the ultrasonic biometric sensing device. An exterior surface of the upper element is an input surface for the biometric sensing device. The biometric sensing device includes discrete ultrasonic transducers, a first electrode layer disposed over a first surface of the discrete ultrasonic transducers, and a second electrode layer disposed over a second surface of the discrete ultrasonic transducers. The first electrode layer includes discrete electrode members. Each discrete electrode member spans two or more discrete ultrasonic transducers. The first surface of the discrete ultrasonic transducers is positioned transverse to the input surface of the biometric sensing device. The second electrode layer includes discrete electrode elements, with a discrete electrode element disposed over the second surface of one ultrasonic transducer. High voltage drive circuitry is operably connected to the first electrode layer, and low voltage readout circuitry is operably connected to the second electrode layer. A processing channel can be operably connected to the readout circuitry.

In yet another aspect, a method of operating the biometric sensing device can include applying a drive signal pulse to at least a portion of the discrete electrode members when an image of a biometric subject is to be captured. Each discrete ultrasonic transducer that is associated with the discrete electrode members that receive the drive signal pulse produces a sound wave pulse based on the drive signal pulse. Signals are read from the associated discrete ultrasonic transducers via the discrete electrode elements. The signals are generated by the associated discrete ultrasonic transducers based on reflected portions of the sound wave pulses. The image of the biometric subject may be constructed based on the signals read from the discrete ultrasonic transducers.

BRIEF DESCRIPTION OF THE DRAWINGS

Embodiments of the invention are better understood with reference to the following drawings. The elements of the drawings are not necessarily to scale relative to each other. Identical reference numerals have been used, where possible, to designate identical features that are common to the figures.

DETAILED DESCRIPTION

Figure 1:
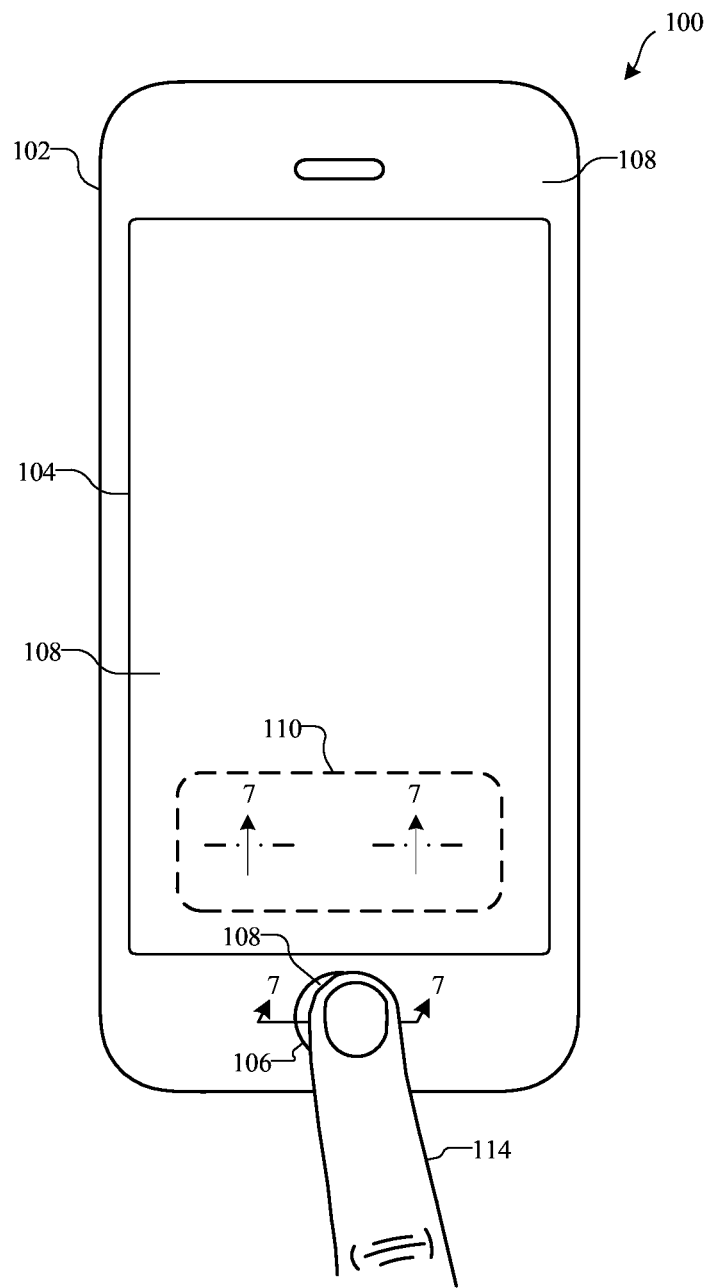
FIG. 1 is a plan view of an example device that is suitable to include an ultrasonic biometric sensing device.

Embodiments described herein provide a biometric sensing device that includes discrete ultrasonic transducers that are used to capture biometric data, such as a fingerprint. A first electrode layer is positioned over a first surface (e.g., top surface) of the discrete ultrasonic transducers. The first electrode layer is formed with multiple discrete electrode members that each spans two or more selected discrete ultrasonic transducers. As one example, each discrete electrode member can span a row of discrete ultrasonic transducers.

A second electrode layer is disposed over a second surface (e.g., bottom surface) of the discrete ultrasonic transducers. The second electrode layer is formed with multiple discrete electrode elements, with a discrete electrode element disposed over one ultrasonic transducer. The discrete electrode elements are operably connected to readout circuitry. At least a portion of the readout circuitry can be included in a substrate positioned below the second electrode layer. In one embodiment, the substrate is configured as an integrated circuit that includes at least a portion of the readout circuitry for the ultrasonic biometric sensing device. In some embodiments, the integrated circuit also includes at least a portion of the processing channel that is operably connected to the readout circuitry. As one example, the integrated circuit may be an application-specific integrated circuit.

Drive circuitry is operably connected to the discrete electrode members. The drive circuitry is configured to generate drive signals that are applied to the ultrasonic transducers through the discrete electrode members. At least a portion of the drive circuitry may be included in a second integrated circuit. The drive circuitry can be electrically connected to the first electrode layer using any suitable technique. For example, in one embodiment conductive lead lines electrically connect the drive circuitry to the first electrode layer.

When an image of a biometric subject (e.g., a finger) is to be captured, the drive circuitry applies a drive signal to one or more discrete electrode members. Based on the drive signal, the ultrasonic transducers operably connected to the one or more discrete electrode members each generate a sound wave pulse. In one embodiment, the sound wave pulses collectively form a plane wave that propagates to the input surface of the ultrasonic biometric sensing device. A fraction of the sound waves reflect off the input surface, and the discrete ultrasonic transducers are used to detect the reflected sound waves. The reflected sound waves create dynamic pressure on the ultrasonic transducers, and respective ultrasonic transducers produce an electrical signal that is proportional to the amount of pressure applied to the transducer. The signals obtained from the discrete ultrasonic transducers are used to construct the image of the biometric subject (e.g., a fingerprint image).

In some embodiments, the drive circuitry is high voltage circuitry that applies a high voltage signal to some or all of the discrete ultrasonic transducers. In one non-limiting example, some or all of the ultrasonic transducers can be driven with a one hundred volt signal for five nanoseconds. The signals read from the discrete ultrasonic transducers are typically low voltage signals, and the readout circuitry therefore operates at a low voltages. As one example, the signals read from the ultrasonic transducers can be measured in microvolts. Because the discrete ultrasonic transducers are positioned between the discrete electrode members and the discrete electrode elements, the discrete ultrasonic transducers can isolate the high voltage drive circuitry and the low voltage readout and processing channel from each other.

Referring now to FIG. 1, there is shown a plan view of an example device that is suitable to include an ultrasonic biometric sensing device. The electronic device 100 includes an enclosure 102, a display 104, and an input/output (I/O) device 106. The electronic device 100 can also include one or more internal components (not shown) typical of a computing or electronic device, such as, for example, one or more processors, memory components, network interfaces, and so on.

In the illustrated embodiment, the electronic device 100 is implemented as a smart telephone. Other embodiments, however, are not limited to this construction. Other types of computing or electronic devices can include an ultrasonic biometric sensing device, including, but not limited to, a netbook or laptop computer, a tablet computing device, a digital camera, a biometric sensing device used in conjunction with, for example, controlled access to a secured building or device, and a wearable electronic or communication device.

As shown in FIG. 1, the enclosure 102 can form an outer surface or partial outer surface and protective case for the internal components of the electronic device 100, and may at least partially surround the display 104. The enclosure 102 can be formed of one or more components operably connected together, such as a front piece and a back piece. Alternatively, the enclosure 102 can be formed of a single piece operably connected to the display 104.

The display 104 can be operably or communicatively connected to the electronic device 100. The display 104 can be implemented with any type of suitable display, such as a retina display, a color liquid crystal display (LCD), or an organic light-emitting display (OLED). The display 104 can provide a visual output for the electronic device 100 and/or function to receive user inputs to the electronic device. For example, the display 104 can be a multi-touch capacitive sensing touchscreen that can detect one or more user touch and/or force inputs.

The I/O device 106 can be implemented with any type of input or output device. By way of example only, the I/O device 106 can be a switch, a button, a capacitive sensor, or other input mechanism. The I/O device 106 allows a user to interact with the electronic device 100. For example, the I/O device 106 may be a button or switch to alter the volume, return to a home screen, and the like. The electronic device can include one or more input device and/or output devices, and each device can have a single I/O function or multiple I/O functions. Example I/O devices include a microphone, speakers, a touch sensor, network or communication ports, a display, and wireless communication devices.

A cover glass 108 can be disposed over some or all of an exterior top surface of the electronic device. In the illustrated embodiment, the cover glass 108 can be a flexible touchable surface that is made of any suitable transparent material, such as, for example, a glass, a plastic, or sapphire. In one embodiment, a cover glass 108 is positioned over the entire top surface of the electronic device (e.g., the enclosure 102, the display 104, and the I/O device 106). In the illustrated embodiment, a region of the cover glass can act as an input surface for the ultrasonic biometric sensing device. As one example, the region of the cover glass 108 over the I/O device 106 may be an input surface for the ultrasonic biometric sensing device. Additionally or alternatively, a region 110 of the cover glass 108 over the display 104 can be an input surface for the ultrasonic biometric sensing device.

The present invention is described herein in conjunction with an ultrasonic fingerprint sensing device, although other embodiments are not limited to a fingerprint sensing device. Images or data obtained from other biometric subjects may be captured in other embodiments.

An ultrasonic fingerprint sensing device can capture fingerprint images when one or more fingers, or a portion of a finger or fingers, is proximate to or touching an input surface of the ultrasonic fingerprint sensing device. For example, as shown in FIG. 1, an ultrasonic fingerprint sensing device may capture images when a finger 114 is near or in contact with the I/O device 106. In other embodiments, an ultrasonic fingerprint sensing device may capture fingerprint images when a finger is near or in contact with the region 110.

As used herein, the terms "image" and "fingerprint image" include an image, a composite image formed with multiple images, and other types of data that can be captured by an ultrasonic fingerprint sensing device. By way of example only, an ultrasonic fingerprint sensing device can produce a data structure that defines the features in a fingerprint. Additionally, the term "fingerprint image" is meant to encompass an image or other data relating to a fingerprint of some or all of one or more fingers, some or all of a palm, some or all of a hand, and various combinations thereof. The term "finger" is meant to encompass one or more fingers or thumbs, some or all of a palm, some or all of a hand, and various combinations thereof.

Figure 2:
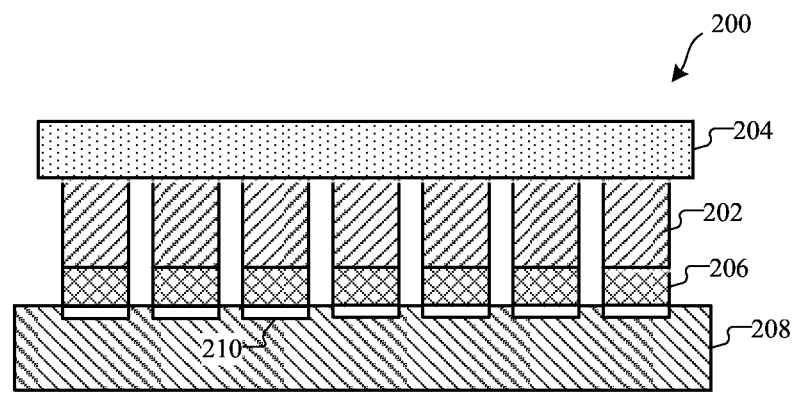
FIG. 2 is a cross-sectional view of one example of an ultrasonic biometric sensing device.

FIG. 2 is a cross-sectional view of one example of an ultrasonic fingerprint sensing device. The ultrasonic fingerprint sensing device 200 includes multiple discrete ultrasonic transducers 202. The discrete ultrasonic transducers 202 can produce a sound wave pulse in response to an electrical stimulus such as a voltage or current. The sound wave pulses propagate to the input surface, where a fraction of the sound wave pulses reflect off the input surface. The discrete ultrasonic transducers may also detect these reflected sound wave pulses. The reflected sound wave pulses create a pressure on the discrete ultrasonic transducers, and a discrete ultrasonic transducer produces an electrical signal that is proportional to the amount of pressure applied to that transducer. In one embodiment, the discrete ultrasonic transducers are made of a material having piezoelectric properties. One example material includes, but is not limited to, a lead zirconate titanate material. A different material having piezoelectric properties can be used in other embodiments.

A first electrode layer 204 is disposed over a first surface (e.g., a top surface) of the discrete ultrasonic transducers 202. A second electrode layer 206 is positioned over a second surface (e.g., bottom surface) of the discrete ultrasonic transducers 202. The first and second electrode layers may be made of any suitable conductive material. For example, the first and second electrode layers can be made of a metal including, for example, silver, copper, and gold. In other embodiments, the first and second electrode layers may be made of a non-metal conductive material, such as indium tin oxide (ITO).

A substrate 208 is positioned below and attached to the second electrode layer 206. In some embodiments, the substrate 208 can act as a support structure for the discrete ultrasonic transducers. In one embodiment, the substrate 208 is configured as an integrated circuit that includes at least a portion of the readout circuitry for the ultrasonic fingerprint sensing device. Additionally, in some embodiments, the integrated circuit may include at least a portion of the processing channel that is operably connected to the readout circuitry. The second electrode layer 206 can electrically connect the ultrasonic transducers to the integrated circuit through a conductive element (e.g., contact pads 210) disposed on the surface of the integrated circuit. The contact pads can be electrically connected to the readout circuitry. One example of a suitable processing channel is described in conjunction with FIG. 8. In one non-limiting example, the integrated circuit is an application-specific integrated circuit (ASIC), but other types of integrated circuits can be used.

Figure 3:
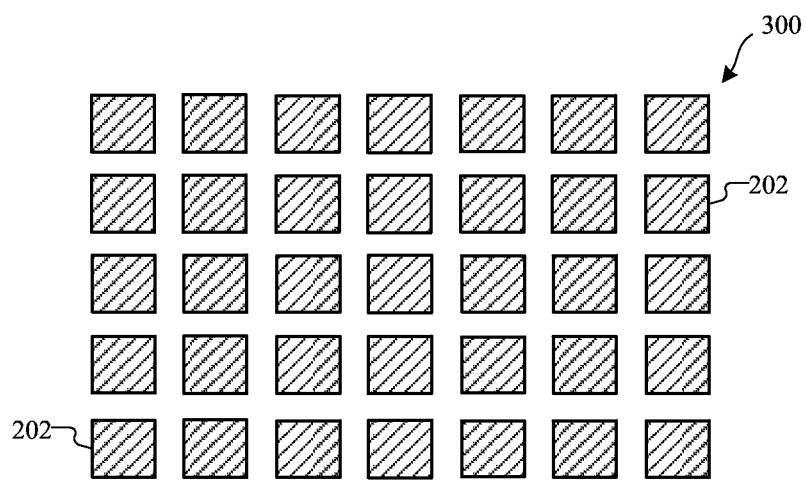
FIG. 3 is a plan view of the discrete ultrasonic transducers shown in FIG. 2.

FIG. 3 is a plan view of the discrete ultrasonic transducers shown in FIG. 2. Each ultrasonic transducer 202 is separate and distinct from the other ultrasonic transducers 202. As shown in FIG. 3, the ultrasonic transducers can be arranged in rows and columns to form an array 300 of ultrasonic transducers. Although FIG. 3 depicts thirty-five discrete ultrasonic transducers, those skilled in the art will recognize that an ultrasonic fingerprint sensing device can include any number of discrete ultrasonic transducers. Additionally, a discrete ultrasonic transducer can have any suitable shape and dimensions. Additionally, the discrete ultrasonic transducers can be arranged in any suitable arrangement and/or orientation. As one example, the ultrasonic transducers may be arranged in two or more concentric circles around a central point or a central ultrasonic transducer.

Figure 4:
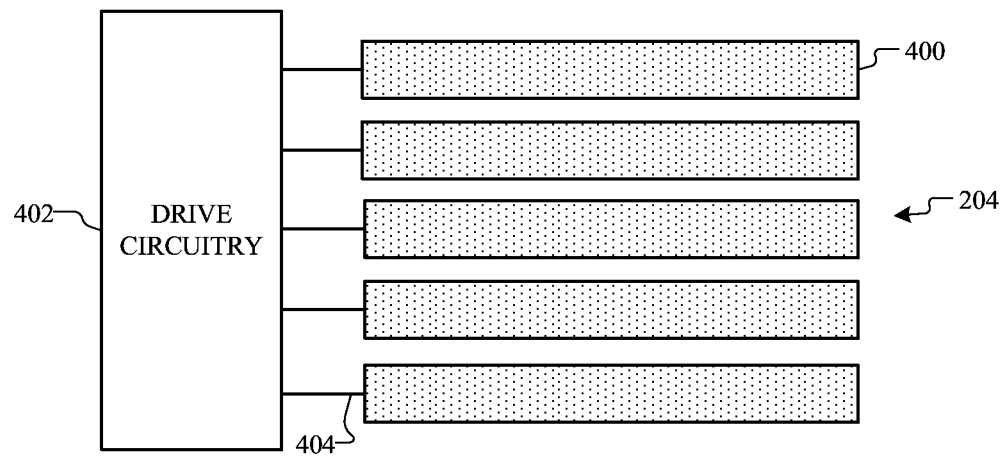
FIG. 4 is a plan view of the first electrode layer 204 shown in FIG. 2 operably connected to drive circuitry.

Referring now to FIG. 4, there is shown a plan view of the first electrode layer 204 shown in FIG. 2 operably connected to drive circuitry. The electrode layer 204 is formed of discrete electrode members 400. Each discrete electrode member spans two or more discrete ultrasonic transducers (e.g., at least a portion of a row or a column of discrete electrode members). The discrete electrode members span or are disposed over multiple discrete ultrasonic transducers. The discrete electrode members 400 can be operably connected to drive circuitry 402 by a conductive element 404. The drive circuitry 402 is configured to generate drive pulses that are applied to the discrete ultrasonic transducers through the discrete electrode members 400. Based on the drive pulse applied to one or more discrete electrode members, the discrete ultrasonic transducers operably connected to the one or more discrete electrode members produce sound wave pulses.

Figure 5:
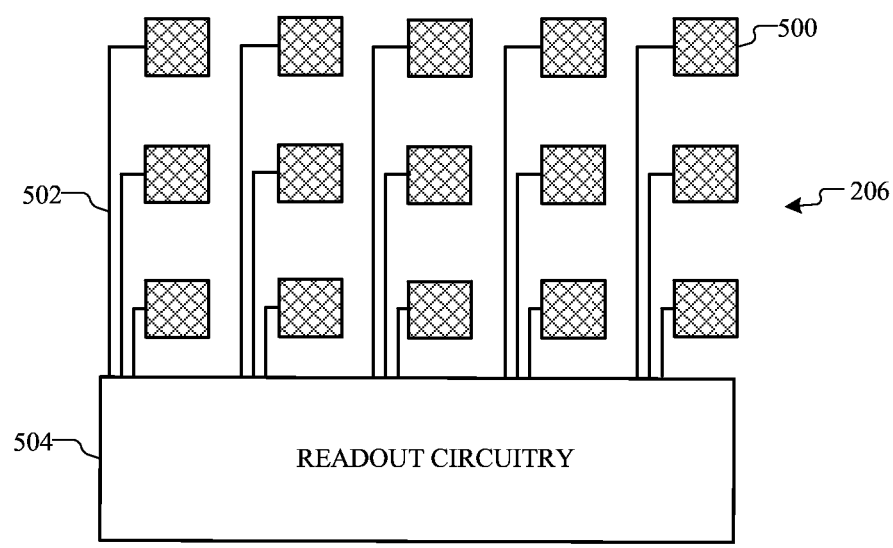
FIG. 5 is a plan view of the second electrode layer 206 shown in FIG. 2 operably connected to readout circuitry.

FIG. 5 is a plan view of the second electrode layer 206 shown in FIG. 2 operably connected to readout circuitry. The second electrode layer 206 is formed of discrete electrode elements 500. Conductive elements 502 represent the electrical connection between the discrete electrode elements 500 and the readout circuitry 504. As described earlier, a fraction of the sound wave pulses reflect off the input surface and are detected by respective discrete ultrasonic transducers. The sound wave pulses apply pressure to the discrete ultrasonic transducers. The piezoelectric material produces an electrical signal that is proportional to the amount of pressure on the piezoelectric material. The readout circuitry 504 reads the electrical signal from one or more ultrasonic transducers.

Figure 6:
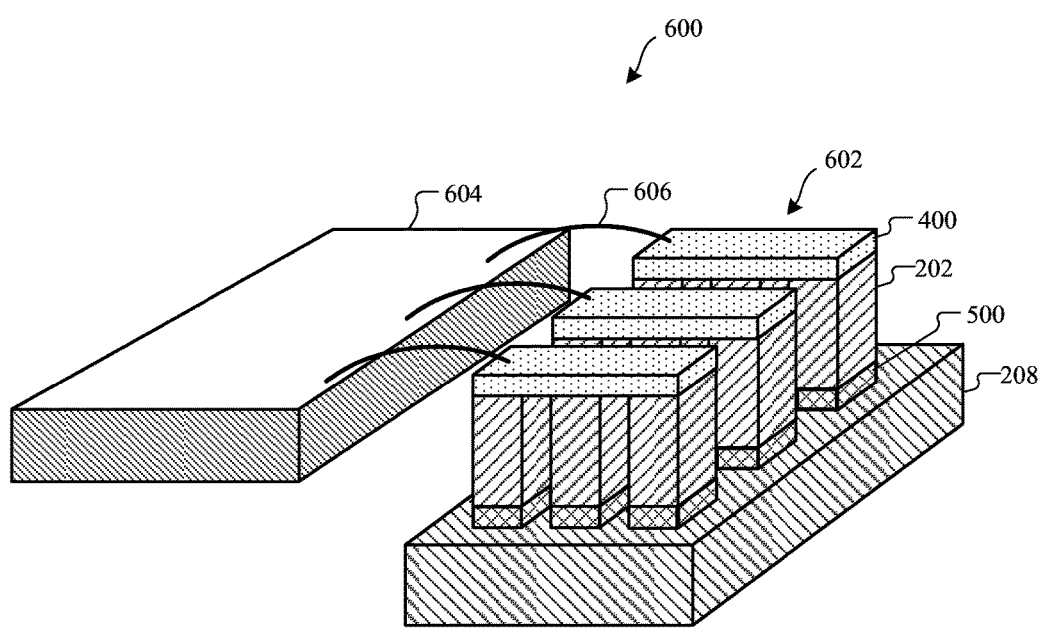
FIG. 6 is a perspective view of one example of an ultrasonic fingerprint sensing system.

Referring now to FIG. 6, there is shown a perspective view an ultrasonic fingerprint sensing system. The ultrasonic fingerprint sensing system 600 includes an ultrasonic fingerprint sensing device 602 that includes the discrete electrode members 400 disposed over a first surface (e.g., top surface) of the discrete ultrasonic transducers 202. The discrete electrode elements 500 are disposed between a second surface (e.g., bottom surface) of the discrete ultrasonic transducers 202 and the substrate 208.

When the substrate 208 is an integrated circuit, the discrete electrode elements 500 can be electrically connected to circuitry in the integrated circuit. As described earlier, at least a portion of the readout circuitry can be included in the substrate 208. Additionally, in some embodiments a portion of the processing channel may be included in the substrate 208. The readout circuitry can be configured to read a signal from select discrete ultrasonic transducers 202 via discrete electrode elements 500.

Drive circuitry can be included in the integrated circuit 604 and electrically connected to the discrete electrode members 400 by conductive elements, such as lead lines 606. The drive circuitry can be configured to apply a drive signal to one or more individual discrete electrode members.

Figure 7A:
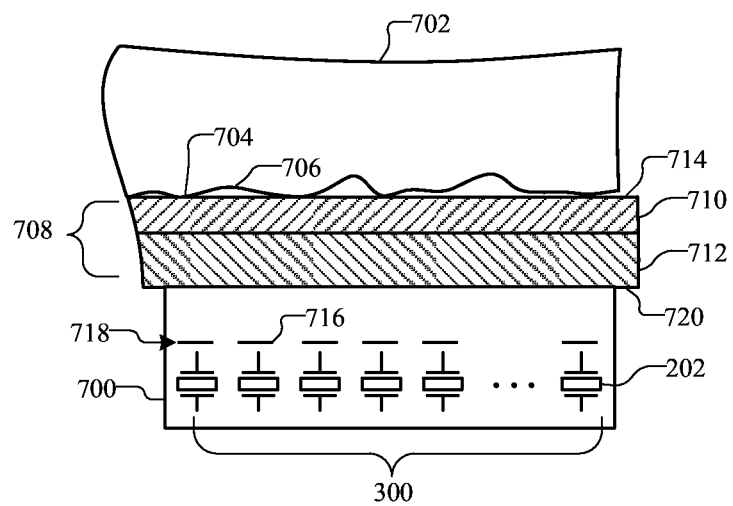
FIGS. 7A-7B are cross-sectional views of the electronic device 100 taken along line 7-7 in FIG. 1.
Figure 7B:
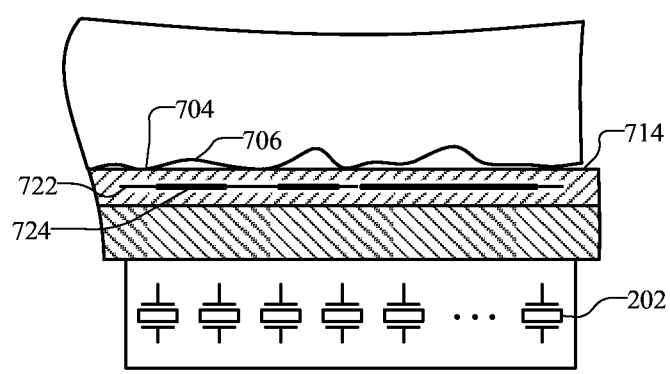

Operation of the ultrasonic fingerprint sensing system is now described. FIGS. 7A-7B are cross-sectional views of the electronic device 100 taken along line 7-7 in FIG. 1. The ultrasonic fingerprint sensing device 700 can capture a fingerprint image of at least a portion of a finger 702 by imaging the ridges 704 and valleys 706 that collectively form a fingerprint. The ultrasonic fingerprint sensing device 700 can be implemented as the ultrasonic biometric sensing device shown in FIG. 2.

In the illustrated embodiment, multiple layers of material are disposed over the ultrasonic fingerprint sensing device 700. The multiple layers of material collectively form an upper element 708. As shown, the upper element 708 includes a top layer 710 and an intermediate layer 712. In other embodiments, the upper element can include one or more layers of material. The top layer 710 receives touch inputs from a user and has a top surface 714 that acts as an input surface for the ultrasonic fingerprint sensing device. In some embodiments, the discrete ultrasonic transducers 202 may be positioned transverse or substantially parallel to the input surface 714.

The upper element 708 can be a portion of a display (e.g., region 110 in FIG. 1), a portion of an input device (e.g., 110 device 106 in FIG. 1), or a portion of the enclosure of the electronic device. The upper element 708 can include active components (e.g., circuits, circuit traces, a display layer, and so on) or passive components (e.g., glass sheet, an adhesive layer, and so on) or a combination thereof.

For example, if the upper element 708 is included in region 110 in FIG. 1, the upper element 708 can include a cover glass (e.g., cover glass 108), a touch sensing device, a polarizing layer, a third conductive layer, a color filter layer, and a display layer such as an LCD or LED display layer. The touch sensing device may be constructed with a first conductive layer, an insulating layer, and a second conductive layer. As another example, if the upper element 708 is included in the I/O device 106 shown in FIG. 1, the upper element 708 may include a cover glass, an ink layer, an adhesive layer, and a flexible circuit that is operably connected to a switch.

When a fingerprint image is to be captured, the drive circuitry 402 applies a drive pulse to the discrete electrode members 400 of the first electrode layer 204 (see FIGS. 4 and 6), which in turn causes the ultrasonic transducers 202 to substantially simultaneously produce a sound wave pulse 716 that collectively form a plane wave 718 that propagates through the upper element 708 from the bottom surface 720 towards the input surface 714. A fraction of the plane wave reflects at each material interface encountered by the plane wave. The plane wave confronts different types of interfaces at the input surface 714. One interface type exists between the top layer 710 and a ridge 704 of the finger 702. Another interface type exists between the top layer 710 and the air residing between the input surface 714 and a valley 706. Different fractions of the plane wave reflect from the different interface types. The fractions of the plane wave(s) that reflect at the two interface types is a function of the differences in acoustic impedance between the two elements at each interface type. The larger the change in acoustic impendence encountered by the plane wave, the larger the fraction of the plane wave reflected.

In other words, the interface at a ridge may reflect a first fraction of the sound waves, while the interface at a valley reflects a different second fraction of the sound waves. The acoustic impedance of skin is higher than the acoustic impedance of air, so the interface at a ridge generally reflects a smaller fraction of the sound waves than the interface at a valley. Since the properties of the reflected sound wave(s) exhibit the same characteristic pattern of the ridges and valleys in the finger, the measurements of the reflected sound waves can be used to construct a fingerprint image.

FIG. 7B depicts the plane wave reflecting off the input surface 714. Different regions of the plane wave (e.g., regions 722 and 724) are depicted with different line thicknesses to illustrate the different fractions of the plane wave reflecting off the different interface types. The fraction 722 of the plane wave reflecting from a location below a ridge 704 is less than the fraction 724 reflecting from a location below a valley 706.

The discrete ultrasonic transducers can be used to detect the reflected sound waves after the discrete ultrasonic transducers produce the plane wave. As described earlier, the reflected sound waves create pressure on the ultrasonic transducers, and the ultrasonic transducers produce an electrical signal that is proportional to the amount of pressure applied to a respective transducer. The readout circuitry 504 can read the signals from the discrete ultrasonic transducers 202 via the discrete electrode elements 500.

Although the plane wave has been described as being formed from a sound wave pulse that is generated by all of the ultrasonic transducers 202, those skilled in the art will recognize that a fingerprint image can be captured using only a portion or portions of the discrete ultrasonic transducers. The drive circuitry 400 can apply drive pulses to select discrete electrode members 400. Similarly, the readout circuitry 500 can individually address and receive signals from select discrete electrode elements 500.

Figure 8:
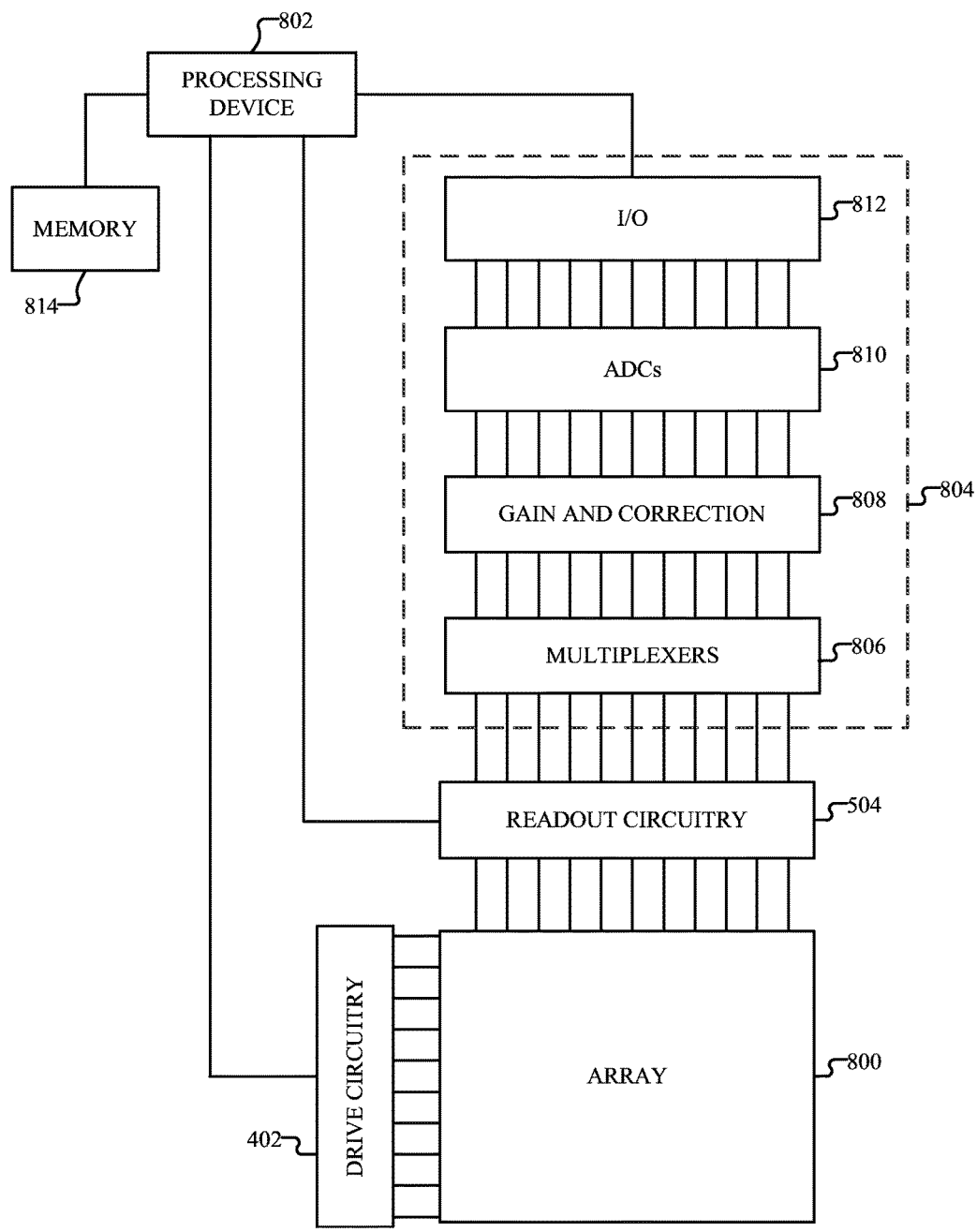
FIG. 8 is a block diagram of an illustrative ultrasonic fingerprint sensing system operably connected to a processing channel.

Referring now to FIG. 8, there is shown a block diagram of an illustrative fingerprint sensing system operably connected to a processing channel. An array 800 of discrete ultrasonic transducers is operably connected to drive circuitry 402 and readout circuitry 504. The array 800 includes N discrete ultrasonic transducers, where N is greater than one. The discrete ultrasonic transducers can be arranged in rows and columns, or in any other given configuration.

As described earlier, the drive circuitry 402 is configured to generate drive pulses that are applied to the ultrasonic transducers via the discrete electrode members 400. Based on the drive pulse, the discrete ultrasonic transducers generate a sound wave pulse. The readout circuitry 504 reads the electrical signal produced by one or more discrete ultrasonic transducers in response to reflected sound waves. Example drive circuitry and readout circuitry are described in more detail in conjunction with FIG. 9.

A processing device 802 is operably connected to the drive circuitry 402 and to the readout circuitry 504. The processing device 802 may be configured to control the timing and operations of the drive circuitry 402 and of the readout circuitry 504. The processing device 802 can be implemented as any electronic device capable of processing, receiving, or transmitting data or instructions. For example, the processing device can be a microprocessor, a central processing unit (CPU), an application-specific integrated circuit (ASIC), a digital signal processor (DSP), or combinations of multiple such devices. As described herein, the term "processing device" is meant to encompass a single processor or processing unit, multiple processors, multiple processing units, or other suitably configured computing element or elements.

A processing channel is operably connected to the readout circuitry 504. An example processing channel 804 is shown in FIG. 8. The illustrated processing channel 804 receives and processes analog signals, digitizes the signals, and outputs the signals to the processing device 802. The processing device 802 is configured to analyze the signals and construct a fingerprint image.

The processing channel 804 can include multiplexer(s) 806 operably connected to the outputs of the readout circuitry 504, gain and correction circuitry 808 operably connected to the outputs of the multiplexer(s) 806, and analog-to-digital converter(s) (ADCs) 810 operably connected to the outputs of the gain and correction circuitry 808. In some embodiments, the gain and correction circuitry is implemented as gain circuitry only, depending on the sampling rate. Example gain circuitry includes, but is not limited to, amplifiers. In some embodiments, the gain and correction circuity may be implemented in-pixel. The term "pixel" refers to one discrete ultrasonic transducer 202. Thus, "in-pixel" refers to a discrete ultrasonic transducer connected to the readout circuitry 504.

In some embodiments, the number of columns in the array of discrete ultrasonic transducers can be greater than the number of analog channels in the processing channel. In such embodiments, a multiplexer is coupled to the input of a gain and correction circuit and configured to multiplex multiple analog signals from associated readout circuitry to a particular ADC.

The ADCs convert the analog signals to digital signals. The outputs of the ADCs 810 are operably connected to input/output (I/O) circuitry 812. Low voltage differential signaling is one example of I/O circuitry. In some embodiments, data formatter circuitry (not shown) may be operably connected between the ADCs 810 and the I/O circuitry 812.

Timing signals and control data for the drive circuitry 402 and/or the readout circuitry 504 can be stored in memory 814. Additionally or alternatively, the signals received by the processing device 802 and/or the fingerprint image may be stored in memory 814. The memory 814 can be configured as any type of memory. By way of example only, memory 814 can be implemented as random access memory, read-only memory, Flash memory, removable memory, or other types of storage elements, in any combination.

Figure 9:
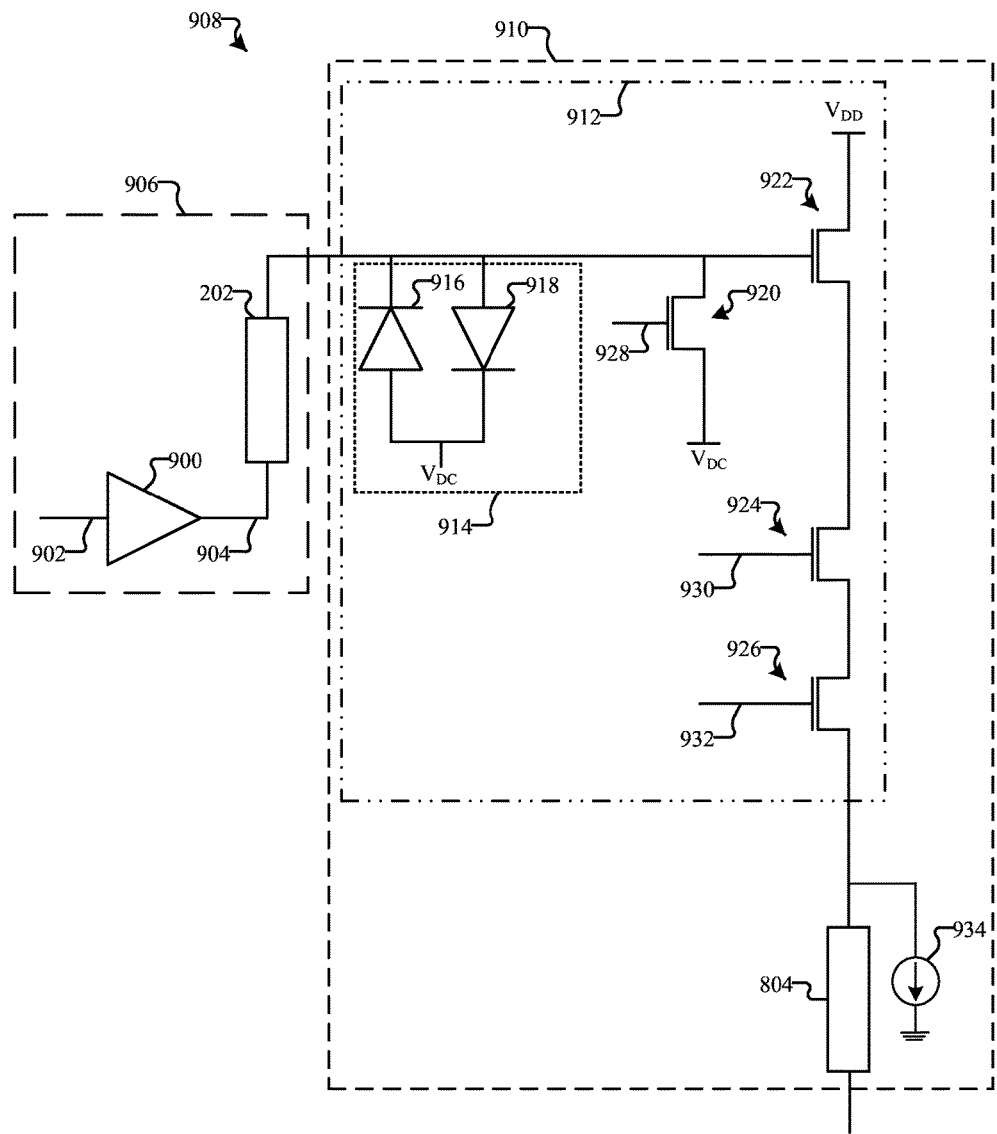
FIG. 9 is a schematic diagram of example of drive circuitry and readout circuitry suitable for use in an ultrasonic fingerprint sensing system.

FIG. 9 is a schematic diagram of example drive circuitry and readout circuitry suitable for use in an ultrasonic fingerprint sensing device. The drive circuitry (e.g., drive circuitry 402 in FIG. 4) includes a driver circuit 900 that receives a control signal on signal line 902 and outputs a high voltage drive pulse on conductive element 904. In one non-limiting example, the high voltage drive pulse is a one hundred volt pulse for five nanoseconds. The high voltage drive pulse is applied to the discrete ultrasonic transducer 202 via the discrete electrode member 400 in the first electrode layer 204 (e.g., discrete electrode members 400 in FIG. 4). In one embodiment, the conductive element may be a lead line electrically connecting the output of the driver circuit 900 to the discrete electrode member (e.g., lead line 606 in FIG. 6).

The driver circuit 900 and the discrete ultrasonic transducer 202 are included in high voltage circuitry 906 of the transducer drive and readout architecture 908. Low voltage circuitry 910 includes the readout circuitry 912 and the processing channel 804. The discrete electrode members 400 in first electrode layer 204 carry high voltage pulses and the discrete electrode elements 500 in the second electrode layer 206 (e.g., discrete electrode elements 500 in FIG. 5) are connected to the low voltage circuitry 910. The discrete ultrasonic transducer 202 can electrically isolate the high low voltage circuitry 906 and the low voltage circuitry 910 from each other.

The illustrative readout circuitry 912 can be included in the readout circuitry 504 shown in FIG. 5. The readout circuitry 912 includes a protection circuit 914 operably connected to the ultrasonic transducer 202. In the illustrated embodiment, the protection circuit 914 includes a first diode 916 and a second diode 918 in a back-to-back arrangement and connected between the ultrasonic transducer 202 and a DC bias $V_{DC}$. One terminal of a drive transistor 920 is connected to the ultrasonic transducer 202 and the other terminal is connected to the DC bias $V_{DC}$. A gate of a readout transistor 922 is electrically connected to the ultrasonic transducer 202. One terminal of the readout transistor 922 is electrically connected to $V_{DD}$, and the other terminal of the readout transistor 922 is connected to a terminal of a first select transistor 924. The other terminal of the first select transistor 924 is connected to a second select transistor 926. The other terminal of the second select transistor 926 is electrically connected to the processing channel 804. In one non-limiting example, $V_{DD}$ can be −0.5 volts and $V_{DC}$ can be $V_{DD}/2$.

The first and second select transistors 924, 926 in the readout circuitry 912 permit a portion of the discrete ultrasonic transducers to be readout out. For example, a portion of the discrete ultrasonic transducers in a row may be read out rather than reading out all of the discrete ultrasonic transducers in the row. In other words, the first and second select transistors 924, 926 allow the discrete ultrasonic transducers to be individually addressable. In other embodiments, one of the select transistors may be omitted from the readout circuitry 912 when signals from groups of discrete ultrasonic transducers are read out (e.g., the discrete ultrasonic transducers associated with an entire row).

Figure 10:
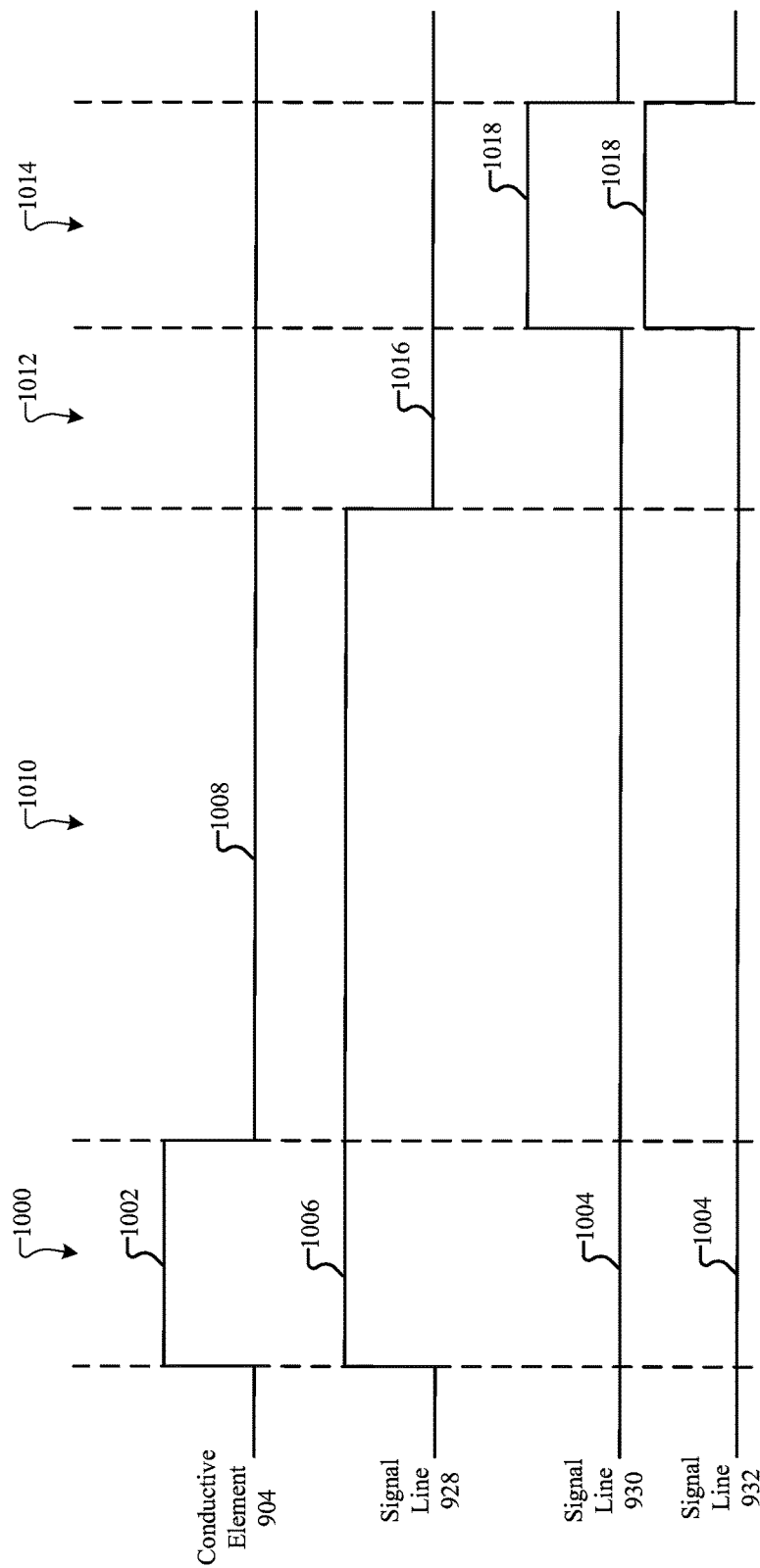
FIG. 10 is a timing diagram suitable for use with the drive and readout circuitry shown in FIG. 9.

The operation of the drive circuitry and the readout circuitry shown in FIG. 9 is described in conjunction with the timing diagram shown in FIG. 10. When a drive pulse is to be applied to the ultrasonic transducer 202 during time period 1000, the high voltage drive pulse is output on conductive element 904 (see 1002). The signal lines 930, 932 electrically connected to the gates of the first and second select transistors 924, 926, respectively, are at a low voltage 1004 (e.g., ground). The signal line 928 electrically connected to the gate of the drive transistor 920 transitions to a high voltage (see 1006) to maintain the low voltage circuitry 910 at a low voltage.

The high voltage pulse on the signal line 904 transitions to a low voltage (see 1008) after time period 1000 and remains at the low voltage during time periods 1010, 1012, and 1014. A sound wave pulse is produced by the ultrasonic transducer 202 during the time period 1000. The signal lines 930, 932 remain at the low voltage during time periods 1010 and 1012. The signal line 928 remains at the high voltage during time period 1010, and transitions to a low voltage (1016) during the transient settling time period 1012. During time period 1014, the signal lines 930, 932 transition to a high voltage (1018) to turn on the first and second transistors 924, 926 and the readout transistor 922 connects to the column bias 934, which provides the current bias for the readout transistor 922 to turn on, and to the processing channel 804. Thus, the signals produced by reflected sound waves during the time period 1014 are readout and processed by the processing channel 804.

It should be noted that embodiments are not limited to the example drive circuitry and readout circuitry shown in FIG. 9. Those skilled in the art will appreciate that the drive circuitry and/or the readout circuitry can be implemented differently. For example, in one embodiment a source follower transistor is used for the readout circuit in FIG. 9. Other embodiments may include, for example, a gain stage or a differential pair.

Figure 11:
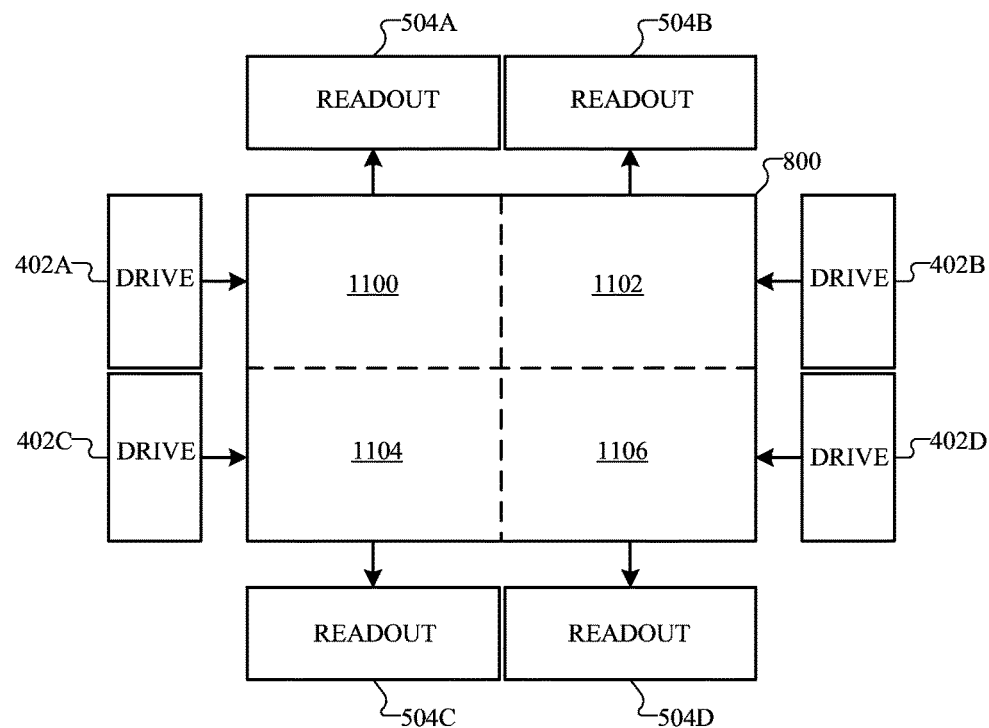
FIGS. 11-12 are block diagrams of different drive and readout architectures for an ultrasonic fingerprint sensing device.
Figure 12:
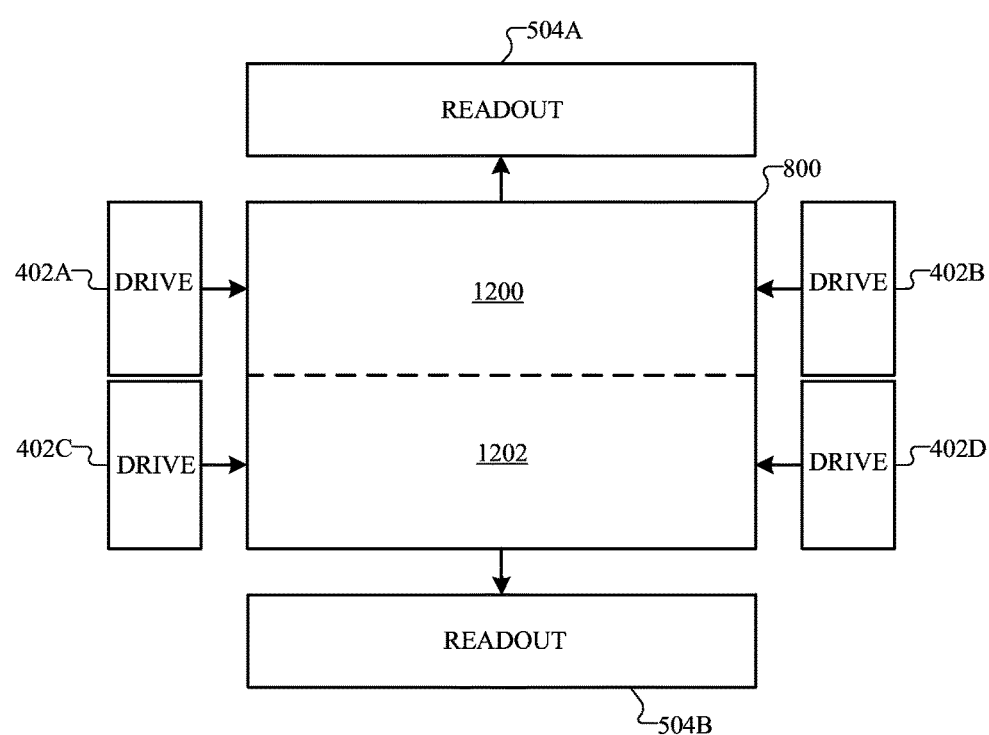

Referring now to FIGS. 11 and 12, there are shown block diagrams of different drive and readout architectures for an ultrasonic fingerprint sensing device. As shown in FIG. 11, the array 800 of discrete ultrasonic transducers is logically divided into four regions 1100, 1102, 1104, 1106. Drive circuitry 402A generates drive pulses for the discrete ultrasonic transducers in region 1100, and readout circuitry 504A reads signals from the discrete ultrasonic transducers in region 1100. Similarly, drive circuitry 402B generates drive pulses for the discrete ultrasonic transducers in region 1102, and readout circuitry 504B reads signals from the discrete ultrasonic transducers in region 1102. Drive circuitry 402C and 402D generate drive pulses for the discrete ultrasonic transducers in regions 1104 and 1106, respectively, and readout circuitry 504C and 504D reads signals from the discrete ultrasonic transducers in the respective regions. Each region 1100, 1102, 1104, and 1106 can be driven and read independent of the other regions.

As shown in FIG. 12, the array 800 of discrete ultrasonic transducers is logically divided into two regions 1200, 1202. Drive circuitry 402A, 402B generates drive pulses for the discrete ultrasonic transducers in region 1200, and readout circuitry 504A reads signals from the discrete ultrasonic transducers in region 1200. Similarly, drive circuitry 402C, 402D generates drive pulses for the discrete ultrasonic transducers in region 1202, and readout circuitry 504B reads signals from the discrete ultrasonic transducers in region 1202. Each region 1200, 1202 can be driven and read independent of the other region. The operations of the drive circuitry connected to a region (e.g., drive circuitry 402A, 402B) are synchronized so that the drive pulses are applied substantially simultaneously to the region.

Dividing the array into two or more regions may reduce the RC time constant of the array 800, and therefore relaxes the design requirements of the system. It should be noted that the number of discrete ultrasonic transducers in each region may be the same or may differ. For example, the number of discrete ultrasonic transducers in all of the regions can differ in each region. As another example, the number of discrete ultrasonic transducers in region 1200 (or regions 1100 and 1102 combined) can be the same but differ from the number of discrete ultrasonic transducers in region 1202 (or regions 1104 and 1106 combined).

Figure 13:
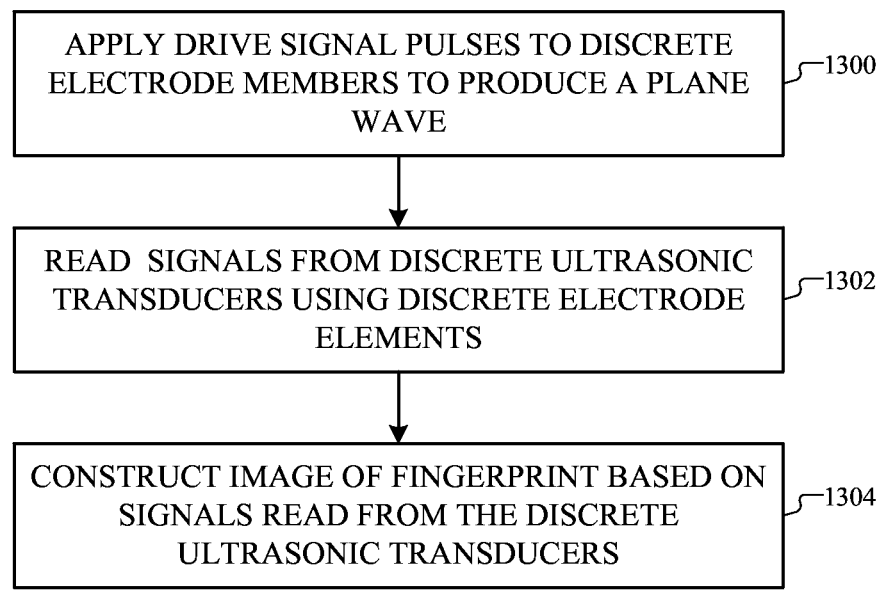
FIG. 13 is a flowchart of a method of operating an ultrasonic fingerprint sensing device.

Referring now to FIG. 13, there is shown a flowchart of a method of operating an ultrasonic fingerprint sensing device. Initially, as shown in block 1300, drive signal pulses are applied to the discrete electrode members to produce a plane wave. As described earlier, the plane wave propagates through the upper element to the input surface and portions of the plane wave reflect from the input surface toward the discrete ultrasonic transducers. The reflected plane wave fractions impinge on the discrete ultrasonic transducers, causing the discrete ultrasonic transducers to generate electrical signals that are proportional to the pressure or force applied to the discrete ultrasonic transducers by the impinging reflected sound waves. The signals are then read from the discrete ultrasonic transducers via the discrete electrode elements (block 1302). A fingerprint image can be constructed based on the signals read from the discrete ultrasonic transducers (block 1304).

Various embodiments have been described in detail with particular reference to certain features thereof, but it will be understood that variations and modifications can be effected within the spirit and scope of the disclosure. Even though specific embodiments have been described herein, it should be noted that the application is not limited to these embodiments. In particular, any features described with respect to one embodiment may also be used in other embodiments, where compatible. Likewise, the features of the different embodiments may be exchanged, where compatible.

We claim:

1. A biometric sensing system, comprising:
   discrete ultrasonic transducers, each discrete ultrasonic transducer comprising a piezoelectric material having a first surface and a second surface opposite the first surface;
   a first electrode layer disposed over the first surface of the discrete ultrasonic transducers, wherein the first electrode layer comprises a plurality of discrete electrode members each spanning two or more discrete ultrasonic transducers;
   a second electrode layer disposed over the second surface of the discrete ultrasonic transducers, wherein the second electrode layer comprises discrete electrode elements with each discrete electrode element disposed over one ultrasonic transducer;
   high voltage drive circuitry operably connected to the first electrode layer; and
   low voltage readout circuitry operably connected to the second electrode layer.

2. The biometric sensing system as in claim 1, wherein at least a portion of the low voltage readout circuitry is included in a first integrated circuit operably connected to the second electrode layer.

3. The biometric sensing system as in claim 1, wherein at least a portion of the high voltage drive circuitry is included in a second integrated circuit operably connected to the first electrode layer.

4. The biometric sensing system as in claim 1, wherein the high voltage drive circuitry comprises a driver circuit operably connected to at least one discrete electrode member in the first electrode layer.

5. The biometric sensing device as in claim 1, wherein the readout circuitry comprises:
   a voltage protection circuit operably connected to at least one discrete electrode element in the second electrode layer;
   a first terminal of a drive transistor operably connected to the at least one discrete electrode element;
   a gate of a readout transistor operably connected to the at least one discrete electrode element; and
   a first terminal of a first select transistor operably connected to a terminal of the readout transistor.

6. The biometric sensing device as in claim 5, further comprising a processing channel operably connected to a second terminal of the first select transistor.

7. The biometric sensing device as in claim 5, further comprising:
a first terminal of a second readout transistor operably connected to a second terminal of the first select transistor;
a processing channel operably connected to a second terminal of the second select transistor; and
a column bias operably connected to the second terminal of the second select transistor.

8. An electronic device, comprising:
a biometric sensing device comprising:
discrete ultrasonic transducers, each discrete ultrasonic transducer comprising a piezoelectric material having a first surface and a second surface opposite the first surface;
a first electrode layer disposed over the first surface of the discrete ultrasonic transducers, wherein the first electrode layer comprises discrete electrode members each spanning two or more discrete ultrasonic transducers;
a second electrode layer disposed over the second surface of the discrete ultrasonic transducers, wherein the second electrode layer comprises discrete electrode elements with one discrete electrode element disposed over one ultrasonic transducer;
an upper element that includes at least one layer of material disposed over the ultrasonic biometric sensing device, wherein an exterior surface of the upper element is an input surface for the biometric sensing device;
high voltage drive circuitry operably connected to the first electrode layer;
low voltage readout circuitry operably connected to the second electrode layer; and
a processing channel operably connected to the low voltage readout circuitry; wherein
each discrete ultrasonic transducer electrically isolates the high voltage drive circuitry from the low voltage readout circuitry.

9. The electronic device as in claim 8, wherein the discrete ultrasonic transducers are positioned transverse to the input surface.

10. The electronic device as in claim 8, further comprising a processing device operably connected to the high voltage drive circuitry.

11. The electronic device as in claim 8, further comprising a processing device operably connected to the low voltage readout circuitry.

12. The electronic device as in claim 8, further comprising a processing device operably connected to the processing channel.

13. The electronic device as in claim 8, wherein at least a portion of the low voltage readout circuitry is included in a first integrated circuit operably connected to the second electrode layer.

14. The electronic device as in claim 8, wherein at least a portion of the high voltage drive circuitry is included in a second integrated circuit operably connected to the first electrode layer.

15. The electronic device as in claim 14, wherein at least a portion of the processing channel is included in the second integrated circuit operably connected to the first electrode layer.

16. The biometric sensing system as in claim 8, wherein the high voltage drive circuitry comprises a driver circuit operably connected to at least one discrete electrode member in the first electrode layer.

17. The electronic device as in claim 8, wherein the readout circuitry comprises:
a voltage protection circuit operably connected to at least one discrete electrode element in the second electrode layer;
a first terminal of a drive transistor operably connected to the at least one discrete electrode element;
a gate of a readout transistor operably connected to the at least one discrete electrode element; and
a first terminal of a first select transistor operably connected to a terminal of the readout transistor, wherein a second terminal of the first select transistor is operably connected to the processing channel.

18. The electronic device as in claim 8, wherein the readout circuitry comprises:
an isolation circuit operably connected to at least one discrete electrode element in the second electrode layer;
a first terminal of a drive transistor operably connected to the at least one discrete electrode element;
a gate of a readout transistor operably connected to the at least one discrete electrode element; and
a first terminal of a first select transistor operably connected to a terminal of the readout transistor; and
a first terminal of a second select transistor operably connected to a second terminal of the first select transistor, wherein a second terminal of the second select transistor is operably connected to a column bias and the processing channel.

19. The electronic device as in claim 8, wherein the processing channel comprises:
multiplexers operably connected to the readout circuitry;
gain and correction circuitry operably connected to the multiplexers; and
analog-to-digital converters operably connected to the gain circuitry.

20. A method of operating a biometric sensing device that includes discrete ultrasonic transducers, a plurality of first discrete electrode members each disposed over a first surface of a piezoelectric substrate of the discrete ultrasonic transducers and spanning two or more discrete ultrasonic transducers, and a second discrete electrode member disposed over a second surface opposite the first surface of the piezoelectric substrate of each discrete ultrasonic transducer, the method comprising:
applying a drive signal pulse to the plurality of first discrete electrode members when an image of a biometric subject is to be captured, wherein each discrete ultrasonic transducer produces a sound wave pulse based on the drive signal pulse;
using the second discrete electrode elements to read signals from the discrete ultrasonic transducers, wherein the signals are generated by the discrete ultrasonic transducers based on reflected portions of the sound wave pulses; and
constructing a biometric image based on the signals read from the discrete ultrasonic transducers.

* * * * *